US012753355B2

(12) United States Patent
Mathur et al.

(10) Patent No.: US 12,753,355 B2
(45) Date of Patent: Oct. 6, 2026

(54) PROCESS FOR CONVERTING OLEFINS TO JET FUEL WITH OLEFIN RECYCLE

(71) Applicant: UOP LLC, Des Plaines, IL (US)

(72) Inventors: Ashish Mathur, Gurgaon (IN); Debanjan Chakrabarti, Arlington Heights, IL (US); Jeannie Mee Blommel, Oregon, WI (US); Richard K. Hoehn, Mount Prospect, IL (US); Joel S. Paustian, Vernon Hills, IL (US); Manuela Serban, Northbrook, IL (US)

(73) Assignee: UOP LLC, Rosemont, IL (US)

( * ) Notice: Subject to any disclaimer, the term of this patent is extended or adjusted under 35 U.S.C. 154(b) by 261 days.

(21) Appl. No.: 18/417,219

(22) Filed: Jan. 19, 2024

(65) Prior Publication Data

US 2024/0247198 A1 Jul. 25, 2024

Related U.S. Application Data

(60) Provisional application No. 63/480,765, filed on Jan. 20, 2023.

(51) Int. Cl.

| | |
|---|---|
| ***C10G 69/12*** | (2006.01) |
| ***C07C 2/02*** | (2006.01) |
| ***C07C 2/04*** | (2006.01) |
| ***C07C 2/06*** | (2006.01) |
| ***C07C 2/08*** | (2006.01) |

(52) U.S. Cl.

CPC .............. *C10G 69/126* (2013.01); *C07C 2/02* (2013.01); *C07C 2/04* (2013.01); *C07C 2/06* (2013.01); *C07C 2/08* (2013.01); *C10G 2300/1088* (2013.01); *C10G 2300/4081* (2013.01); *C10G 2400/08* (2013.01)

(58) Field of Classification Search

CPC .......... C10G 69/126; C10G 2300/1088; C10G 2300/4081; C10G 2400/08; C10G 50/00; C10G 57/02; C07C 2/02; C07C 2/04; C07C 2/06; C07C 2/08

See application file for complete search history.

(56) References Cited

U.S. PATENT DOCUMENTS

| | | | | |
|---|---|---|---|---|
| 4,487,985 A * | 12/1984 | Tabak | C07C 2/12 | 585/533 |
| 4,749,820 A * | 6/1988 | Kuo | C07C 11/02 | 585/533 |
| 2012/0197053 A1* | 8/2012 | Cantrell | C10L 1/04 | 585/329 |
| 2014/0134059 A1* | 5/2014 | Nicholas | C10G 69/126 | 422/142 |
| 2014/0135543 A1* | 5/2014 | Nicholas | C10G 57/02 | 585/533 |
| 2015/0157998 A1* | 6/2015 | Luebke | B01D 3/143 | 422/187 |

(Continued)

*Primary Examiner* — Ali Z Fadhel

(74) *Attorney, Agent, or Firm* — Paschall & Associates, LLC; James C. Paschall

(57) ABSTRACT

A process for oligomerizing olefins to distillate fuels which oligomerizes a recycle olefin stream with a charge olefin stream in a first-stage oligomerization reactor. The first-stage oligomerate is oligomerized in a second-stage oligomerzation reactor to provide a second-stage oligomerate stream. A recycle olefin stream is taken from said second-stage oligomerate stream.

23 Claims, 5 Drawing Sheets

(56) References Cited

U.S. PATENT DOCUMENTS

| | | | | |
|---|---|---|---|---|
| 2015/0159099 | A1* | 6/2015 | Luebke ................ | C10G 69/126<br>585/315 |
| 2015/0166428 | A1* | 6/2015 | Krupa .................... | C10G 50/00<br>585/517 |
| 2015/0376082 | A1* | 12/2015 | Nicholas ................ | C10G 50/00<br>585/315 |
| 2016/0312134 | A1* | 10/2016 | Fichtl ................... | C10G 69/126 |

* cited by examiner

PROCESS FOR CONVERTING OLEFINS TO JET FUEL WITH OLEFIN RECYCLE

FIELD

The field is the conversion of olefins to distillate. The field may particularly relate to oligomerizing olefins to distillate fuels.

BACKGROUND

Molecular sieves such as microporous crystalline zeolite and non-zeolitic catalysts, particularly silicoaluminophosphates (SAPO), are known to promote the conversion of oxygenates such as methanol to light olefins. The highly efficient Methanol to Olefin (MTO) process may convert oxygenates to light olefins and was typically considered for plastics production. Light olefins produced from the MTO process are highly concentrated in ethylene and propylene and also contain significant concentrations of butenes, pentenes, and hexenes. When methanol derived from low carbon intensity feedstocks such as carbon dioxide or municipal solid waste is fed to an MTO unit, renewable light olefins are produced.

Ethylene can be dimerized and oligomerized into olefins such as C4, C6 and C8 olefins. Propylene can be dimerized and oligomerized into olefins such as C6, C9 and C12 olefins. Ethylene and propylene can be co-oligomerized into olefins such as C5 and C7 olefins. Olefin oligomerization is an exothermic process that can oligomerize smaller olefins into larger olefins. More specifically, it can convert olefins including oligomerized olefins into a distillate including jet fuel and diesel range products. The oligomerized distillate can be saturated for use as transportation fuels.

Unlike automobile engines, jet engines cannot be replaced easily by electrical motor systems because a high energy density is required to fuel planes which cannot be supplied with batteries. Large incentives are currently available for renewable jet fuel in certain regions. Other regions have announced planned mandates for renewable jet fuel to be gradually implemented in the coming decades to meet carbon dioxide emission reduction targets.

An efficient process is desired for converting renewable olefinic feeds to distillate fuels.

BRIEF SUMMARY

We have formulated a process for oligomerizing an olefin stream to distillate fuel. The process comprises oligomerizing a charge olefin stream and a recycle olefin stream with a first-stage oligomerization catalyst to produce a first-stage oligomerized olefin stream. The first-stage oligomerized olefin stream is oligomerized with a second-stage oligomerization catalyst to provide a second-stage oligomerized stream. The recycle olefin stream is taken from the second-stage oligomerized stream.

DEFINITIONS

Figure 1:
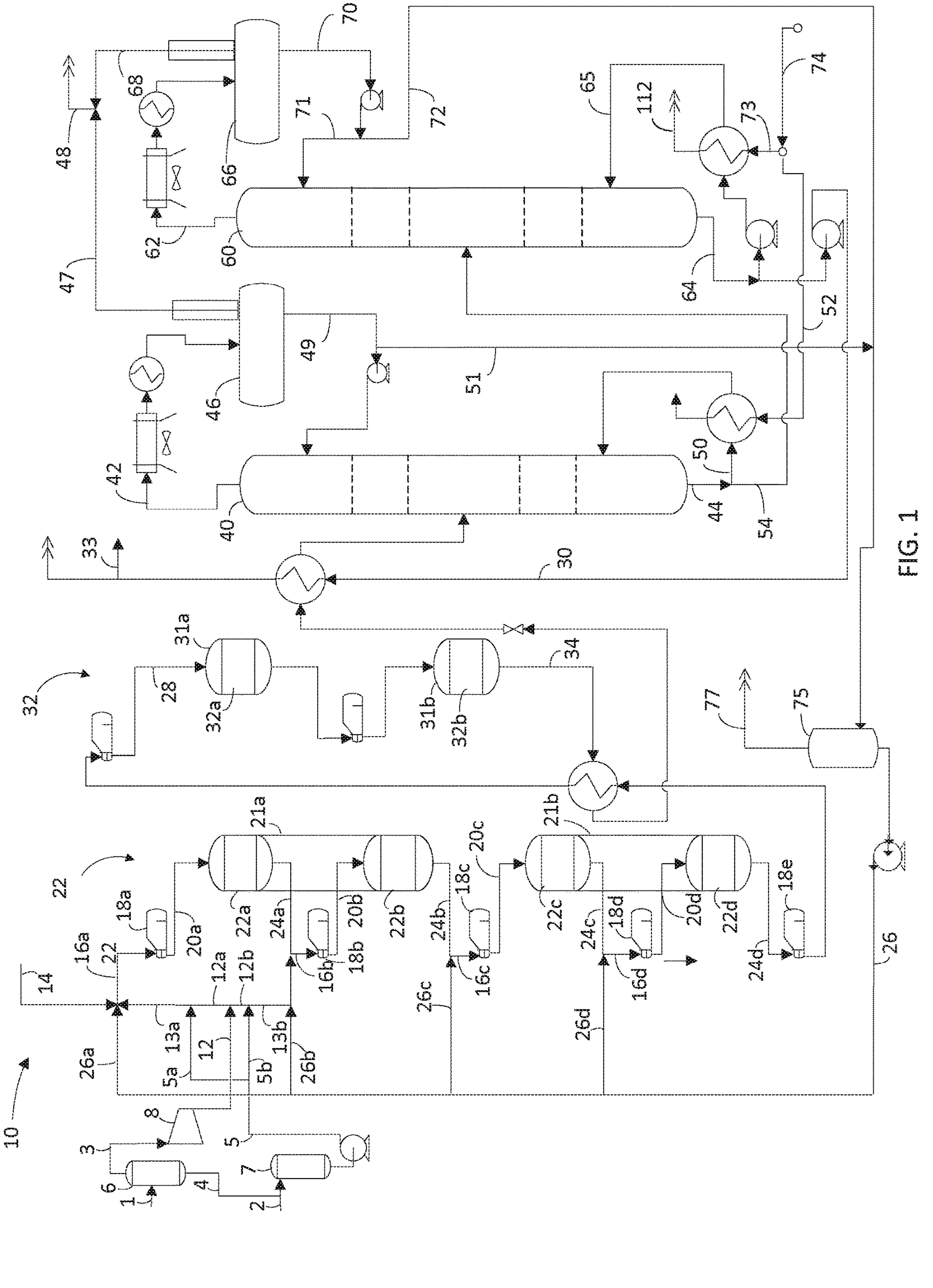
FIG. 1 is a schematic drawing of an oligomerization section of a process and apparatus of the present disclosure.

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripping columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure. As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

As used herein, the term "True Boiling Point" (TBP) means a test method for determining the boiling point of a material which corresponds to ASTM D-2892 for the production of a liquefied gas, distillate fractions, and residuum of standardized quality on which analytical data can be obtained, and the determination of yields of the above fractions by both mass and volume from which a graph of temperature versus mass % distilled is produced using fifteen theoretical plates in a column with a 5:1 reflux ratio.

As used herein, the term "T5", "T90" or "T95" means the temperature at which 5 mass percent, 90 mass percent or 95 mass percent, as the case may be, respectively, of the sample boils using ASTM D-86 or TBP.

As used herein, the term "initial boiling point" (IBP) means the temperature at which the sample begins to boil using ASTM D-7169, ASTM D-86 or TBP, as the case may be.

As used herein, the term "end point" (EP) means the temperature at which the sample has all boiled off using ASTM D-7169, ASTM D-86 or TBP, as the case may be.

As used herein, the term "diesel" means hydrocarbons boiling in the range of an IBP between about 125° C. (257° F.) and about 175° C. (347° F.) or a T5 between about 150° C. (302° F.) and about 200° ° C. (392° F.) and the "diesel cut point" comprising a T95 between about 343° C. (650° F.) and about 399° C. (750° F.) using the TBP distillation method or a T90 between 280° ° C. (536° F.) and about 340° ° C. (644° F.) using ASTM D-86. The term "green diesel" means diesel comprising hydrocarbons not sourced from fossil fuels.

As used herein, the term "jet fuel" means hydrocarbons boiling in the range of a T10 between about 190° ° C. (374° F.) and about 215° C. (419° F.) and an end point of between about 290° ° C. (554° F.) and about 310° C. (590° F.). The term "green jet fuel" means jet fuel comprising hydrocarbons not sourced from fossil fuels.

DETAILED DESCRIPTION

The process disclosed involves oligomerizing an olefin stream comprising ethylene and/or propylene. The olefin stream may comprise larger (C4-C8) olefins. We have found that C2-C3 alkanes can be produced in the oligomerization process that requires removal in a dealkanizer column. An olefin splitter column can be used to recover lighter olefins for recycle to the oligomerization process. The process and apparatus may include an oligomerization section 10 illustrated in FIG. 1 and a hydrogenation section 110 as illustrated in FIG. 2.

Figure 2:
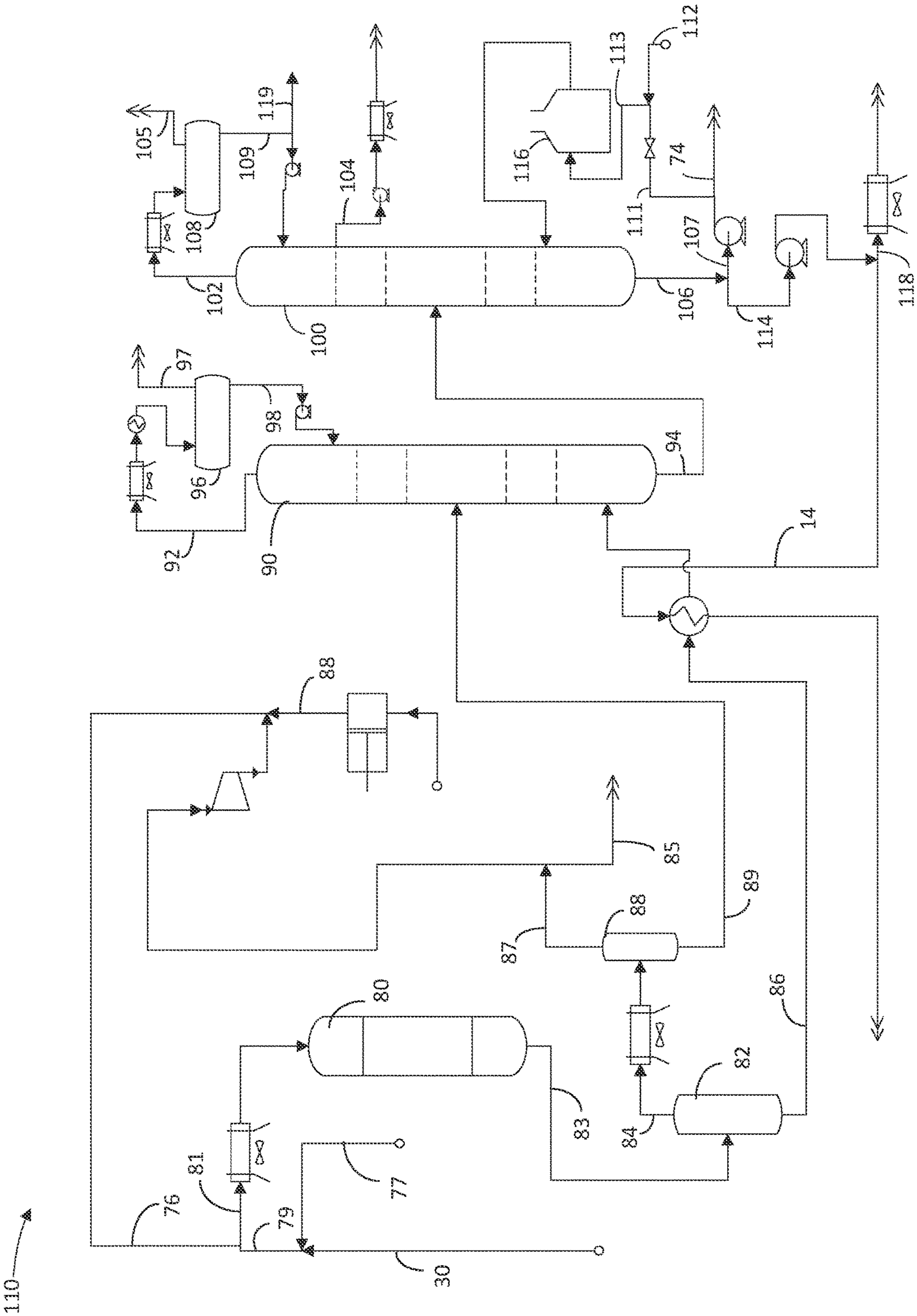
FIG. 2 is a schematic drawing of a hydrogenation section of a process and apparatus of the present disclosure.

Turning to the oligomerization section 10 of FIG. 1, a preliminary vapor olefin stream in line 1 comprising C2 olefins is fed to a preliminary separator 6. The preliminary vapor olefin stream is separated in the preliminary separator to provide a vapor olefin stream in line 3 and a liquefied olefin stream in line 4. The preliminary separator may olefin be operated at a temperature of about 16° C. (60° F.) to about 38° C. (100° F.) and a pressure of about 2.1 MPa (g) (300 psig) to about 2.8 MPa (g) (400 psig). The vapor olefin stream in line 3 may be compressed in a compressor 8 up to oligomerization pressure in line 12.

A preliminary liquid olefin stream in line 2 comprising C3+ olefins is provided to the oligomerization section 10. The preliminary olefin stream may comprise C3-C8 olefins. The preliminary olefin stream in line 2 may be combined with the liquefied olefin stream in line 4 which may comprise C3-C8 olefins and fed to a liquid feed surge drum 7. A liquid olefin stream in line 5 from the liquid feed surge drum 7 comprising C3-C8 liquid olefins may be combined with the compressed vapor olefin stream in line 11 to provide a vapor olefin stream in line 12.

The vapor and liquid olefin streams may comprise substantial ethylene and propylene. The vapor and liquid olefin streams may predominantly comprise ethylene and/or propylene. In an aspect, the vapor and liquid olefin streams may comprise at least 95 mol % ethylene and/or propylene. The vapor and liquid olefin streams in lines 5 and 12 may be styled light olefin streams. Additional olefinic species with carbon numbers ranging from C4 to C8 can be expected in the charge streams. The light olefin streams may be provided by the dehydration of ethanol or provided from a MTO unit. The light olefin streams may be at a temperature of about 20° C. (68° F.) to about 150° C. (302° F.) and a pressure of about 2.16 MPag (350 psig), preferably about 3.5 MPag (500 psig), to about 8.4 MPag (1200 psig).

The light olefin streams may be initially contacted with a first-stage oligomerization catalyst to oligomerize the ethylene and propylene to oligomers and then contacted with a second oligomerization catalyst to oligomerize unconverted ethylene and propylene from the first-stage oligomerization.

The oligomerization reaction generates a large exotherm. For example, dimerization of ethylene can generate 612 kcal/kg (1100 BTU/lb) of heat. Consequently, this large exotherm must be managed. Accordingly, the light olefin streams in lines 5 and 12 may each be split into multiple olefin streams. In FIG. 1, the light olefin streams are each split into two separate streams. The compressed vapor olefin stream in line 12 may be split into a first vapor olefin stream in line 12*a* and a second vapor olefin stream in 12*b*. The liquid olefin stream in line 5 is split into a first liquid olefin stream in line 5*a* and a second liquid olefin stream in line 5*b*. The first vapor olefin stream in line 12*a* is mixed with the first liquid olefin stream in line 5*a* to provide a first charge olefin stream in a first charge olefin line 13*a*. The second vapor olefin stream in line 12*a* is mixed with the second liquid olefin stream in line 5*b* to provide the second charge olefin stream in a second charge olefin line 13*b*. More or less separate multiple olefin streams may be used. Up to six charge olefin streams are readily contemplated.

The compressed vapor olefin stream in line 12 may be split into equal aliquot multiple olefin streams in lines 12*a* and 12*b*. The liquid olefin stream in line 5 may be split into equal aliquot multiple olefin streams in lines 5*a* and 5*b*. Alternatively, the compressed vapor olefin stream in line 12 may be split into unequal streams. Similarly, the liquid olefin stream in line 5 may be split into unequal streams. For example, either or both of the vapor olefin stream or the liquid olefin stream may be split into streams of descending flow rates in which a charge olefin stream to a preceding reactor has a larger flow rate than a charge olefin stream to a subsequent reactor. In an embodiment, both of the vapor olefin stream or the liquid olefin stream may be split into two streams of equal flow rates, each comprising 50 vol % of the charge olefin stream.

In another embodiment, the first charge olefin stream in the first charge olefin line 13*a* may comprise about 70 to about 90 vol % of the charge olefin streams and the second charge olefin streams in the second olefin line 13*b* may comprise about 10 to about 30 vol % of the charge olefin streams. In another embodiment, each of the charge streams are split in different proportions. For example, liquid olefin stream in line 5 can be split into two streams such that the first liquid stream in line 5*a* would comprise 70 to 90% of the liquid olefin stream in line 5 and the second liquid stream in line 5*b* would comprise of 10 to 30% of the liquid olefin stream, while compressed vapor stream in line 12 would be split equally into two streams such that both the first vapor olefin stream in line 12*a* and the second olefin stream in line 12*b* comprise of 50% of the compressed vapor olefin stream.

To manage the exotherm, the charge olefin stream may be diluted with a diluent stream to provide a diluted olefin stream to absorb the exotherm. The diluent stream may comprise a paraffin stream in a diluent line 14. The diluent stream in the diluent line 14 may be added to the first charge olefin stream in the first charge olefin line 13*a* before they are charged to the first-stage oligomerization reactor 22. Preferably, the diluent stream is added to the first charge olefin stream in line 13*a* after the splits of the charge olefin streams in line 5 and 12 into multiple olefin streams to provide a first diluted olefin charge stream in line 16*a*, so the diluent stream passes through all of the first-stage oligomerization reactions. Alternatively, the diluent stream may also be split into multiple streams with each diluent stream added to one or more of a corresponding charge olefin stream. The diluent stream may have a mass flow rate of about 2 to about 8 times and preferably about 3 to about 6 times the combined mass flow rates of the first charge olefin stream in the first charge olefin line 13*a* and the second charge olefin stream in the second charge olefin line 13*b*.

A recycle olefin stream in a recycle line 26 comprising C4 to C8 olefins may be mixed with the charge olefin stream and oligomerized in the first-stage oligomerization reactor 22. In an embodiment, the recycle olefin stream in line 26 is split into a plurality of recycle olefin streams 26*a*-26*d*. A recycle olefin stream in a first recycle olefin line 26*a* may be mixed with the first charge olefin stream in line 13*a* and charged to the first-stage oligomerization reactor 22. In a further embodiment, the first recycle olefin stream in the first recycle olefin line 26*a* is mixed with the first charge olefin stream in line 13*a* and the diluent stream in line 14 to provide a diluted first charge olefin stream in line 16*a*.

The first diluted charge olefin stream may comprise no more than 50 wt % olefins, suitably no more than 30 wt % olefins and preferably no more than 20 wt % olefins. In an embodiment, the first diluted olefin stream comprises about 10 to about 35 wt % C2 to C8 olefins. The first diluted olefin stream may comprise no more than 50 wt % ethylene, suitably no more than 25 wt % ethylene and preferably no more than 20 wt % ethylene. In an embodiment, the first diluted charge olefin stream comprises about 10 to about 20 wt % propylene. The first diluted charge olefin stream may comprise no more than 50 wt % propylene, suitably no more than 25 wt % propylene and preferably no more than 20 wt % propylene. In an embodiment, the first diluted charge olefin stream comprises about 10 to about 20 wt % propylene.

The first-stage oligomerization reactor 22 may comprise a series of first-stage oligomerization catalyst beds 22*a*, 22*b*, 22*c* and 22*d* each for charging with olefin charge streams. The first-stage oligomerization 22 reactor preferably contains four fixed first-stage oligomerization catalyst beds 22*a*, 22*b*, 22*c* and 22*d*. It is also contemplated that each first-stage oligomerization catalyst bed 22*a*, 22*b*, 22*c* and 22*d* may be in a dedicated first-stage oligomerization reactor or multiple first-stage oligomerization catalyst beds may be in two or more separate first-stage oligomerization reactor vessels. Up to six, first-stage oligomerization catalyst beds are readily contemplated. In FIG. 1, two, first stage oligomerization reactor vessels 21*a* and 21*b* are utilized.

A parallel first-stage oligomerization reactor may be used when the first-stage oligomerization reactor 22 has deactivated during which the first-stage oligomerization reactor 22 is regenerated in situ by combustion of coke from the catalyst. In another embodiment, each first-stage oligomerization reactor may comprise a lead reactor, a lag reactor and a spare reactor to facilitate regeneration. Only two reactor vessels 21*a*, 21*b* are shown in FIG. 1.

The diluted first charge olefin stream in line 16*a* may be cooled in a first charge cooler 18*a* to provide a cooled diluted first charge olefin stream in line 20*a* and charged to a first bed 22*a* of first-stage oligomerization catalyst in the first, first-stage oligomerization reactor vessel 21*a* of the first-stage oligomerization reactor 22. The cooled diluted first charge olefin stream in line 20*a* may be charged at a temperature of about 180° C. (356° F.) to about 260° C. (500° F.) and a pressure of about 3.5 MPag (500 psig) to about 8.4 MPag (1200 psig). The charge cooler 18*a* may comprise a steam generator.

The diluted first charge olefin stream may be charged to the first, first-stage catalyst bed 22*a* in line 20*a* preferably in a down flow operation. However, upflow operation may be suitable. The diluted first charge olefin stream is in a mixed vapor-liquid phase in which the vapor phase predominantly comprises ethylene. As oligomerization of ethylene, propylene and recycle olefins occurs in the first, first-stage oligomerization catalyst bed 22*a*, an exotherm is generated due to the highly exothermic nature of the olefin oligomerization reaction.

Oligomerization of the first charge olefin stream produces a first oligomerized effluent stream in a first oligomerized effluent line 24*a* at an elevated outlet temperature despite the cooling and dilution. The elevated outlet temperature is limited to between 150° C. (302° F.) and about 260° C. (500° F.).

The second charge olefin stream in line 13*b* may be mixed with a second recycle olefin stream in a second recycle olefin line 26*b* and with the first oligomerized effluent stream in the first oligomerized effluent line 24*a* removed from the first, first-stage oligomerization catalyst bed 22*a* in the first, first-stage reactor 21*a* to provide a mixed second charge olefin stream in line 16*b*. The first oligomerized effluent stream in line 24*a* includes the diluent stream from diluent line 14 added to the first charge olefin stream in line 13*a*. The second charge olefin stream may comprise no more than 35 wt % C2 to C8 olefins, suitably no more than 25 wt % C2 to C8 olefins and preferably no more than 20 wt % C2 to C8 olefins. The second charge olefin stream may comprise no more than 30 wt % ethylene, suitably no more than 25 wt % ethylene and preferably no more than 20 wt % ethylene. The second charge olefin stream may comprise no more than 30 wt % propylene, suitably no more than 25 wt % propylene and preferably no more than 20 wt % propylene. The second mixed charge olefin stream in line 16*b* may be cooled in a second charge cooler 18*b* which may be located externally to the first, first-stage oligomerization reactor 21*a* to provide a cooled second charge olefin stream in line 20*b* and charged to a second bed 22*b* of first-stage oligomerization catalyst in the first, first-stage oligomerization reactor 21*a*. The charge cooler 18*b* may comprise a steam generator.

The second cooled charge olefin stream in line 20*b* may be charged at a temperature of about 180° ° C. (356° F.) to about 230° C. (446° F.) and a pressure of about 3.5 MPag (500 psig) to about 8.4 MPag (1200 psig). The second cooled charge olefin stream will include diluent and olefins from the first oligomerized stream. The diluted second charge olefin stream is in a mixed vapor-liquid phase in which the vapor phase predominantly comprises ethylene. The olefins from the first oligomerized stream will oligomerize in the second, first-stage catalyst bed 22*b*. Oligomerization of ethylene, propylene, recycle olefins and oligomers in the second olefin stream in the second, first-stage oligomerization catalyst bed 22*b* produces a second oligomerized olefin effluent stream in a second oligomerized effluent line 24*b* at an elevated outlet temperature. The elevated outlet temperature may be limited to between 30° C. (54° F.) and about 50° ° C. (90° F.) above the inlet temperature to the catalyst bed 22*b*.

The second oligomerized effluent stream in line 24*b* removed from the second, first-stage oligomerization catalyst bed 22*b* in the first, first-stage reactor vessel 21*a* may be mixed with a third recycle olefin stream in a third recycle olefin line 26*c* to provide a first recycle olefin charge stream in line 16*c*. In an embodiment, none of the first charge olefin stream in line 13*a* and the second charge olefin stream in line 13*b* is directly added to the first recycle olefin charge stream in line 16*c*. Alternatively, a portion of the charge olefin streams in lines 13*a* and 13*b* may be charged with the second oligomerized effluent stream with the first recycle olefin charge stream in line 16*c*. The second oligomerized effluent stream in line 24*b* includes the diluent stream from diluent line 14 added to the first charge olefin streams in line 13*a*. The first recycle olefin charge stream in line 16*c* may comprise no more than 30 wt % ethylene, suitably no more than 25 wt % ethylene and preferably no more than 20 wt % ethylene. The first recycle olefin charge stream may comprise no more than 30 wt % propylene, suitably no more than 25 wt % propylene and preferably no more than 20 wt % propylene. The first recycle olefin charge stream in line 16*c* may comprise no more than 30 wt % C2 to C8 olefins, suitably no more than 25 wt % C2 to C8 olefins and preferably no more than 20 wt % C2 to C8 olefins. The first recycle olefin charge stream in line 16*c* may be cooled in a third charge cooler 18*c* which may be located externally to the oligomerization reactor 22 to provide a cooled first recycle olefin charge stream in line 20*c* and charged to a third bed 22*c* of first-stage oligomerization catalyst in the first-stage oligomerization reactor 22. In an embodiment, the third bed 22*c* of first-stage oligomerization catalyst is provided in a second, first-stage oligomerization reactor vessel 21*b*. The charge cooler 18*c* may comprise a steam generator.

The cooled first recycle olefin charge stream in line 20*c* may be charged at a temperature of about 180° C. (356° F.) to about 230° C. (446° F.) and a pressure of about 3.5 MPag (500 psig) to about 8.4 MPag (1200 psig). The first recycle olefin charge stream will include diluent and olefins from the second oligomerized olefin stream and the third recycle olefin stream. The olefins will oligomerize in the third catalyst bed 22*c*. Oligomerization of ethylene and propylene and oligomerization of oligomers in the first recycle olefin charge stream in the third bed 22*c* of first-stage oligomerization catalyst produces a third oligomerized effluent stream in a third oligomerized effluent line 24*c* at an elevated outlet temperature. In an embodiment, the third oligomerized effluent stream is a penultimate oligomerized effluent stream and the third oligomerized effluent line 24*c* is a penultimate oligomerized effluent line 24*c*. The elevated outlet temperature is limited to between 30° ° C. (54° F.) and about 50° C. (90° F.) above the inlet temperature to the catalyst bed 22*c*.

The third oligomerized effluent stream in line 24*c* removed from the second, first-stage oligomerization reactor vessel 21*b* of the first-stage oligomerization reactor 22 may be mixed with the fourth recycle olefin stream in line 26*d* to provide a second recycle olefin charge stream in line 16*d*. The third oligomerized effluent stream in line 24*c* includes the diluent stream from diluent line 14 added to the first olefin stream in line 13*a*. None of the charge olefin streams in lines 13*a* and 13*b* is directly added to the second recycle olefin charge stream in line 16*d*. In an embodiment, the third oligomerized effluent stream in line 24*c* may also be mixed with a portion of the charge olefin streams in lines 13*a* and 13*b* and be oligomerized therewith. The second recycle olefin charge stream may comprise no more than 35 wt % C2 to C8 olefins, suitably no more than 30 wt % C2 to C8 olefins and preferably no more than 25 wt % C2 to C8 olefins. The second recycle olefin charge stream may comprise no more than 30 wt % ethylene, suitably no more than 25 wt % ethylene and preferably no more than 20 wt % ethylene. The second recycle olefin charge stream may comprise no more than 30 wt % propylene, suitably no more than 25 wt % propylene and preferably no more than 20 wt % propylene. The second recycle olefin charge stream in line 16*d* may be cooled in a fourth charge cooler 18*d* which may be located externally to the second vessel 21*b* of the first-stage oligomerization reactor 22 to provide a cooled second recycle olefin charge stream in line 20*d* and charged to a fourth bed 22*d* of first-stage oligomerization catalyst in the second vessel of the first-stage oligomerization reactor 22. The charge cooler 18*d* may comprise a steam generator.

The cooled second recycle olefin charge stream in line 20*d* may be charged at a temperature of about 180° C. (356° F.) to about 230° C. (446° F.) and a pressure of about 3.5 MPa (g) (500 psig) to about 8.4 MPa (g) (1200 psig). The cooled second recycle olefin charge stream in line 20*d* will include diluent and olefins from the third or penultimate oligomerized effluent stream and C4-C8 olefins from the fourth recycle olefin stream. The olefins will oligomerize over the fourth catalyst bed 22*d*. Oligomerization of ethylene and propylene in the second recycle olefin charge stream in the fourth bed 22*d* of first-stage oligomerization catalyst produces a fourth oligomerized stream in a fourth oligomerized effluent line 24*d* at an elevated outlet temperature. The elevated outlet temperature is limited to between 30° C. (54° F.) and about 50° ° C. (90° F.) above the inlet temperature to the catalyst bed 22*d*.

The fourth oligomerized effluent stream in line 24*d* exits the second reactor vessel 21*b* of the first-stage oligomerization reactor 22. In an embodiment, the fourth oligomerized effluent stream in line 24*d* is a last oligomerized effluent stream, and the fourth oligomerized effluent line 24*d* is a last oligomerized effluent line 24*d*.

The first-stage oligomerization reaction takes place predominantly in the liquid phase or in a mixed liquid and gas phase at a WHSV of 0.5 to 10 $hr^{-1}$ on an olefin basis. We have found that across the first-stage oligomerization catalyst beds, typically 10-50 wt % ethylene in the olefin stream converts to higher olefins. The ethylene will initially dimerize over the catalyst to butenes. A predominance of the propylene and butenes in the olefins stream charged to a first-stage oligomerization catalyst bed is oligomerized. In an embodiment, at least 99 mol % of propylene and butenes in the olefins stream are oligomerized.

The first-stage oligomerization catalyst may include a zeolitic catalyst. The first-stage oligomerization catalyst may be considered a solid acid catalyst. The zeolite may comprise between about 5 and about 95 wt % of the catalyst, for example between about 5 and about 85 wt %. Suitable zeolites include zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. Three-letter codes indicating a zeotype are as defined by the Structure Commission of the International Zeolite Association and are maintained at http://www.iza-structure.org/databases. UZM-8 is as described in U.S. Pat. No. 6,756,030. In a preferred aspect, the first-stage oligomerization catalyst may comprise a zeolite with a framework having a ten-ring pore structure. Examples of suitable zeolites having a ten-ring pore structure include TON, MTT, MFI, MEL, AFO, AEL, EUO and FER. In a further preferred aspect, the first-stage oligomerization catalyst comprising a zeolite having a ten-ring pore structure may comprise a uni-dimensional pore structure. A uni-dimensional pore structure indicates zeolites containing non-intersecting pores that are substantially parallel to one of the axes of the crystal. The pores preferably extend through the zeolite crystal. Suitable examples of zeolites having a ten-ring uni-dimensional pore structure may include MTT. In a further aspect, the first-stage oligomerization catalyst comprises an MTT zeolite.

The first-stage oligomerization catalyst may be formed by combining the zeolite with a binder, and then forming the catalyst into pellets. The pellets may optionally be treated with a phosphorus reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

One of the components of the catalyst binder utilized in the present invention is alumina. The alumina source may be any of the various hydrous aluminum oxides or alumina gels such as alpha-alumina monohydrate of the boehmite or pseudo-bochmite structure, alpha-alumina trihydrate of the gibbsite structure, beta-alumina trihydrate of the bayerite structure, and the like. A suitable alumina is available from UOP LLC under the trademark VERSAL. A preferred alumina is available from Sasol North America Alumina Product Group under the trademark CATAPAL. This material is an extremely high purity alpha-alumina monohydrate (pseudo-bochmite) which after calcination at a high temperature has been shown to yield a high purity gamma-alumina.

A suitable first-stage oligomerization catalyst is prepared by mixing proportionate volumes of zeolite and alumina to achieve the desired zeolite-to-alumina ratio. In an embodiment, the MTT content may about 5 to about 85, for example about 20 to about 82 wt % MTT zeolite, and the balance alumina powder will provide a suitably supported catalyst. A silica support is also contemplated.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260° C. (500° F.) to about 815° C. (1500° F.). The MTT catalyst is not selectivated to neutralize acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 μm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

In one exemplary embodiment, an MTT-type zeolite catalyst disposed on a high purity pseudo bochmite alumina substrate in a ratio of about 90/10 to about 20/80 and preferably between about 20/80 and about 50/50 is provided in a catalyst bed or more in the first-stage oligomerization reactor 22.

The first-stage oligomerization catalyst can be regenerated upon deactivation. Suitable regeneration conditions include subjecting the first-stage oligomerization catalyst, for example, in situ, to hot air at about 400 to about 500° ° C. To facilitate regeneration without downtime, a swing bed arrangement may be employed with an alternative first-stage oligomerization reactor. A regeneration gas stream may be admitted to the first-stage oligomerization reactor 22 requiring regeneration. The regeneration gas may comprise air with an increased or decreased concentration of oxygen. Activity and selectivity of the regenerated catalyst is comparable to fresh catalyst.

The zeolite catalyst is advantageous as a first-stage oligomerization catalyst. The zeolitic catalyst has relatively low sensitivity towards oxygenates contamination. Consequently, a smaller degree of removal of oxygenates is required of olefinic feed in line 1 if produced from an alcohol dehydration process.

The last first-stage oligomerized stream in the last first-stage oligomerized effluent line **24*d* has an increased concentration of ethylene and propylene oligomers compared to the light olefin streams in lines 5 and 12. The last first-stage oligomerized stream in the last first-stage oligomerized effluent line 24*d* is cooled by steam generation in a steam generator 18*e* or by other heat exchange and further cooled by heat exchange against a second stage oligomerized stream in line 34 and perhaps further cooled such as by a steam generator to provide a charge first-stage oligomerized stream and charged to a second-stage oligomerization reactor 32 in a second-stage oligomerization charge line 28. To achieve the most desirable olefin product, the second-stage oligomerization reactor 32 is operated at a temperature from about 80° ° C. (176° F.) to about 200° ° C. (392° F.). The second-stage oligomerization reactor 32** is run at a pressure from about 2.1 MPa (300 psig) to about 7.6 MPa (1100 psig), and more preferably from about 3.5 MPa (500 psig) to about 6.9 MPa (1000 psig). The second-stage oligomerization charge stream oligomerizes in a mixed vapor-liquid phase to predominantly C4+ olefins.

The second-stage oligomerization reactor 32 may be in downstream communication with the first-stage oligomerization reactor 22. The second-stage oligomerization reactor 32 preferably operates in a down flow operation. However, upflow operation may be suitable. The second-stage oligomerization charge stream is contacted with the second-stage oligomerization catalyst causing the unconverted ethylene from the first-stage oligomerization reactor 22 to dimerize and trimerize while higher olefins also dimerize, trimerize and tetramerize to provide distillate range olefins. With regard to the second-stage oligomerization reactor 32, process conditions may be selected to produce a higher percentage of jet range olefins which, when hydrogenated in a subsequent step as will be described below, result in a desirable jet-range hydrocarbon product. The predominance of the unconverted ethylene from the first-stage oligomerization reactor 22 is dimerized, trimerized and tetramerized.

In an embodiment, at least 99 wt % of ethylene in the second-stage oligomerization charge stream is converted to mostly butenes.

The second-stage oligomerization reactor 32 may comprise a first reactor vessel 31*a* comprising a first bed 32*a* of second-stage oligomerization catalyst and a second reactor vessel 31*b* comprising a second bed 32*b* of second-stage oligomerization catalyst. A first, second-stage oligomerized stream is discharged from the first, second-stage reactor vessel 31*a*, cooled and charged to the second, second-stage reactor vessel 31*b*. A second-stage oligomerized stream with an increased average carbon number greater than the charge second-stage oligomerized stream in line 28 exits the second-stage oligomerization reactor 32 in line 34.

The first-stage oligomerization reactor 22 and the second-stage oligomerization reactor 32 may utilize vapor-liquid distribution trays to mix and disperse the ethylene vapor with liquid olefin and liquid paraffin to promote heat transfer and manage the exotherm.

The second-stage oligomerization catalyst is preferably an amorphous silica-alumina base with a metal from either Group VIII and/or Group VIB in the periodic table using Chemical Abstracts Service notations. In an aspect, the catalyst has a Group VIII metal promoted with a Group VIB metal. Typically, the silica and alumina will only be in the base, so the silica-to-alumina ratio will be the same for the catalyst as for the base. The metals can either be impregnated onto or ion exchanged with the silica-alumina base. Co-mulling is also contemplated. Catalysts for the present invention may have a Low Temperature Acidity Ratio of at least about 0.15, suitably of about 0.2, and preferably greater than about 0.25, as determined by Ammonia Temperature Programmed Desorption (Ammonia TPD) as described hereinafter. Additionally, a suitable catalyst will have a surface area of between about 50 and about 400 $m^2/g$ as determined by nitrogen BET.

The preferred second-stage oligomerization catalyst comprises an amorphous silica-alumina support. One of the components of the catalyst support utilized in the present invention is alumina. The alumina may be any of the various hydrous aluminum oxides or alumina gels such as alpha-alumina monohydrate of the bochmite or pseudo-bochmite structure, alpha-alumina trihydrate of the gibbsite structure, beta-alumina trihydrate of the bayerite structure, and the like. A particularly preferred alumina is available from Sasol North America Alumina Product Group under the trademark CATAPAL. This material is an extremely high purity alpha-alumina monohydrate (pseudo-bochmite) which after calcination at a high temperature has been shown to yield a high purity gamma-alumina. Another component of the catalyst support is an amorphous silica-alumina. A suitable silica-alumina with a silica-to-alumina ratio of 2.6 is available from CCIC, a subsidiary of JGC, Japan.

Another component utilized in the preparation of the second-stage oligomerization catalyst utilized in the present invention is a surfactant. The surfactant is preferably admixed with the hereinabove described alumina and the silica-alumina powders. The resulting admixture of surfactant, alumina and silica-alumina is then formed, dried and calcined as hereinafter described. The calcination effectively removes by combustion the organic components of the surfactant but only after the surfactant has dutifully performed its function in accordance with the present invention. Any suitable surfactant may be utilized in accordance with the present invention. A preferred surfactant is a surfactant selected from a series of commercial surfactants sold under the trademark "Antarox" by Solvay S. A. The "Antarox" surfactants are generally characterized as modified linear aliphatic polyethers and are low-foaming biodegradable detergents and wetting agents.

A suitable silica-alumina mixture is prepared by mixing proportionate volumes silica-alumina and alumina to achieve the desired silica-to-alumina ratio. In an embodiment, about 75 to about 99 wt-% amorphous silica-alumina with a silica-to-alumina ratio of 2.6 and about 10 to about 20 wt-% alumina powder will provide a suitable support. In an embodiment, other ratios of amorphous silica-alumina to alumina may be suitable.

Any convenient method may be used to incorporate a surfactant with the silica-alumina and alumina mixture. The surfactant is preferably admixed during the admixture and formation of the alumina and silica-alumina. A preferred method is to admix an aqueous solution of the surfactant with the blend of alumina and silica-alumina before the final formation of the support. It is preferred that the surfactant be present in the paste or dough in an amount from about 0.01 to about 10 wt-% based on the weight of the alumina and silica-alumina.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried.

The paste or dough may be prepared in the form of shaped particulates, with the preferred method being to extrude the dough mixture of alumina, silica-alumina, surfactant and water through a die having openings therein of desired size and shape, after which the extruded matter is broken into extrudates of desired length and dried. A further step of calcination may be employed to give added strength to the extrudate. Generally, calcination is conducted in a stream of dry air at a temperature from about 260° C. (500° F.) to about 815° C. (1500° F.).

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 μm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

Typical characteristics of the amorphous silica-alumina supports utilized herein are a total pore volume, average pore diameter and surface area large enough to provide substantial space and area to deposit the active metal components. The total pore volume of the support, as measured by conventional mercury porosimeter methods, is usually about 0.2 to about 2.0 cc/gram, preferably about 0.25 to about 1.0 cc/gram and most preferably about 0.3 to about 0.9 cc/gram. Ordinarily, the amount of pore volume of the support in pores of diameter greater than 100 angstroms is less than about 0.1 cc/gram, preferably less than 0.08 cc/gram, and most preferably less than about 0.05 cc/gram. Surface area, as measured by the B.E.T. method, is typically above 50 $m^2$/gram, e.g., above about 200 $m^2$/gram, preferably at least 250 $m^2$/gram, and most preferably about 300 $m^2$/gram to about 400 $m^2$/gram.

To prepare the second-stage oligomerization catalyst, the support material is compounded, as by a single impregnation or multiple impregnations of a calcined amorphous refractory oxide support particles, with one or more precursors of at least one metal component from Group VIII or VIB of the periodic table. The Group VIII metal, preferably nickel, should be present in a concentration of about 0.5 to about 15 wt-% and the Group VIB metal, preferably tungsten, should be present in a concentration of about 0 to about 12 wt-%. The impregnation may be accomplished by any method known in the art, as for example, by spray impregnation wherein a solution containing the metal precursors in dissolved form is sprayed onto the support particles. Another method is the multi-dip procedure wherein the support material is repeatedly contacted with the impregnating solution with or without intermittent drying. Yet other methods involve soaking the support in a large volume of the impregnation solution or circulating the support therein, and yet one more method is the pore volume or pore saturation technique wherein support particles are introduced into an impregnation solution of volume just sufficient to fill the pores of the support. On occasion, the pore saturation technique may be modified, so as to utilize an impregnation solution having a volume between about 10 percent less and about 10 percent more than that which will just fill the pores.

If the active metal precursors are incorporated by impregnation, a subsequent or second calcination at elevated temperatures, as for example, between 399° C. (750° F.) and 760° ° C. (1400° F.), converts the metals to their respective oxide forms. In some cases, calcinations may follow each impregnation of individual active metals. A subsequent calcination yields a catalyst containing the active metals in their respective oxide forms.

A preferred second-stage oligomerization catalyst of the present invention has an amorphous silica-alumina base impregnated with about 0.5 to about 15 wt-% nickel in the form of 3.175 mm (0.125 inch) extrudates and a density of about 0.45 to about 0.65 g/ml. It is also contemplated that metals can be incorporated onto the support by other methods such as ion-exchange and co-mulling.

The second-stage oligomerization catalyst can be regenerated upon deactivation. Suitable regeneration conditions include subjecting the catalyst, for example, in situ, to hot air at about 400 to about 500° C. To facilitate regeneration without downtime, a swing bed arrangement may be employed with an alternative second-stage oligomerization reactor. The regeneration gas may comprise air with an increased or decreased concentration of oxygen. Activity and selectivity of the regenerated catalyst is comparable to fresh catalyst.

Second-stage oligomerization reactions are also exothermic in nature. The last oligomerized olefin stream in line **24*d* includes the diluent stream from diluent line 14 added to the first charge olefin stream in the first charge olefin line 13*a* and carried through the first-stage oligomerization catalyst beds 22*a*-22*d*. The diluent stream is then transported into the second-stage oligomerization reactor 32 in line 28 to absorb the exotherm in the second-stage oligomerization reactor. A dedicated diluent line to the second-stage oligomerization reactor 32 is also contemplated for prompt control of exotherm rise or to cool down the second-stage oligomerization reactor 32**.

When the oligomerization reaction is performed according to the above-noted process conditions, a C4 olefin conversion of greater than or equal to about 95% is achieved, or greater than or equal to 97%. The resulting second-stage oligomerized stream in line 34 includes a plurality of olefin products that are distillate range hydrocarbons.

An oligomerized olefin stream in line 34 with an increased C8+ olefin concentration compared to the charge second-stage oligomerization stream in line 28 is heat exchanged with the first-stage oligomerized stream in line **24*d*, let down in pressure, subsequently heat exchanged with an olefin splitter bottoms stream in line 30 and fed to a dealkanizer column 40. The oligomerized olefin stream in line 34** is at a temperature from about 160° ° C. (320° F.) to about 190° C. (374° F.) and a pressure of about 3.9 MPa (gauge) (550 psig) to about 7 MPa (gauge) (1000 psig).

We have found that light alkanes such as ethane and/or propane are generated in the first-stage oligomerization reactor 22 and/or the second-stage oligomerization reactor 32 which must be removed from the second-stage oligomerized stream for fuels production particularly to facilitate light olefin recycle to the first-stage oligomerization reactor 22. Light alkanes are inert and would accumulate in the recycle loop. Hence, the second-stage oligomerized stream in line 34 is dealkanized by fractionation in a dealkanizer column 40 to provide a light alkane stream and a dealkanized stream. In an embodiment, the light alkane stream is an ethane stream in which case the dealkanizer column 40 is a deethanizer column. In another embodiment, the light alkane stream is a propane stream in which case the dealkanizer column 40 is a depropanizer column. The light alkane stream may contain ethane and/or propane and can also be a mixture of ethane and propane.

In the dealkanizer column 40, light alkanes such as C3− and suitably C2− hydrocarbons, are separated perhaps in a light alkane overhead stream in an overhead line 42 from perhaps a dealkanized bottoms stream in a bottoms line 44 comprising C4+ and suitably C3+ hydrocarbons. Olefins may be recycled to the first-stage oligomerization reaction 22 from the dealkanizer overhead stream in the overhead line 42. The dealkanizer column 40 may be operated at a bottoms temperature of about 177° C. (350° F.) to about 302° C. (575° F.) and an overhead pressure of about 207 kPa (gauge) (30 psig) to about 690 kPa (gauge) (100 psig) if operated as a deethanizer column. The dealkanizer column 40 may be operated at a bottoms temperature of about 194° C. (381° F.) to about 333° ° C. (630° F.) and an overhead pressure of about 207 kPa (gauge) (30 psig) to about 1.38 MPa (gauge) (200 psig) if operated as a dealkanizer column.

The light alkane overhead stream in the overhead line 42 may be cooled and separated in a dealkanizer receiver 46 to provide a dealkanized off-gas stream in an off-gas line 47 in which it may be chilled and fed to further processing such as to be taken as fuel gas in line 48 along with a net vapor stream in a receiver overhead line 68. Condensate from the dealkanizer receiver 46 may be refluxed back to the dealkanizer column 40 in a dealkanizer overhead liquid line 49. The dealkanized off-gas stream may be used as fuel for providing heating duty in the process 10. In an embodiment, some of the condensate from the dealkanizer receiver 44 in line 49 may be taken as olefin recycle in line 51 to the first stage oligomerization reactor in lines 72 and 26.

The dealkanized stream perhaps in the bottoms line 44 may be split between a reboil stream in line 50 which is reboiled by heat exchange with a first hot diesel stream in line 52 perhaps taken from a jet fractionator bottom heat exchange stream in the jet bottoms heat exchange line 74 and a net bottoms stream in line 54 which is fed directly to an olefin splitter column 60 perhaps without heating. The reboiled bottom stream in line 50 may be returned boiling to the dealkanizer column 40 to provide heating requirements. In another embodiment, feed to dealkanizer column 40 is not preheated by olefin splitter bottoms stream in line 30, but the feed to the olefin splitter column 60 in the net bottoms line 54 would be preheated by heat exchange with the olefin splitter bottoms stream in line 64.

The dealkanized stream in the dealkanizer net bottoms line 54 is split by fractionation in an olefin splitter column 60 into a light olefin stream perhaps in an olefin splitter overhead line 62 and a heavy olefin stream perhaps in an olefin splitter bottoms line 64. Olefins may be recycled to the first-stage oligomerization reaction 22 from the olefin splitter overhead stream in the overhead splitter overhead line 62. The olefin splitter overhead stream may be chilled to about 19° ° C. (66° F.) to about 93° ° C. (200° F.) and a resulting condensate portion refluxed from an olefin splitter receiver 66 back to the olefin splitter column 60. The net vapor stream in the receiver overhead line 68 from the olefin splitter receiver 66 may be further processed such as fuel gas in line 48 along with the off-gas stream in the off-gas line 47. The light olefin condensate from a bottom of the olefin splitter receiver in line 70 may be split between a reflux stream that is refluxed back to the column in line 71 and a light olefin recycle stream in a recycle line 72 that may be recycled to the first-stage oligomerization reactor 22 or alternatively to the second-stage oligomerization reactor 32. The light olefin stream in line 72 may comprise about 1 to about 15 wt % or perhaps a predominance of the light olefin stream in line 70. The light olefin stream in line 72 may comprise about 40 to about 80 wt % C4-C8 olefins. In an embodiment, the light olefin stream in line 72 may be flashed in a knock-out drum 75 to remove vapors in a light olefin vapor stream which may be transported to the hydrogenation section in an overhead line 77 and the liquid recycle olefin oligomer stream in line 26 may be recycled to the first-stage oligomerization reactor 22 to oligomerize the C4-C8 olefins.

The heavy olefin stream in the splitter bottoms line 64 may be split between a reboil stream in a splitter reboil line 65 that is reboiled by heat exchange with a second hot diesel stream in line 73 perhaps taken from the jet fractionator bottom heat exchange stream in the jet bottoms heat exchange line 74 from FIG. 2 and fed back to the olefin splitter column 60. The cooled second hot diesel stream in line 112 is returned back to the hydrogenation section 110 in FIG. 2 to be reboiled and fed back to the jet fractionation column 100. The heavy olefin stream in the net bottoms line 30 is cooled by heat exchange with the second-stage oligomerized stream in line 34 before it is transported to the hydrogenation section that is not shown. A purge of the heavy olefin stream may be taken in line 33. The heavy olefin stream comprises C9+ olefins that once cooled can be transported to the hydrogenation section 110.

Turning to the hydrogenation section 110 in FIG. 2, the heavy olefin stream in the net olefin splitter bottoms line 30 from FIG. 1 comprising distillate-range C9+ oligomerized olefins may be hydrogenated to saturate the olefinic bonds in a hydrogenation reactor 80 to provide fuels. This step is performed to ensure the product fuel meets or exceeds the thermal oxidation requirements specified in ASTM D7566-20 for Alcohol to Jet Synthesized Paraffinic Kerosene (ATJ-SPK). Additionally, hydrogenating the oligomerized heavy olefins will provide the paraffin stream that may be used as the diluent stream in line 14. The heavy olefin stream in line 30 may be cooled to produce steam and be combined with the light olefin liquid stream comprising C2 to C8 olefins in line 77 also from FIG. 1 to produce a combined olefin stream in line 79. The combined olefin stream in line 79 may also be combined with a hydrogen stream in line 76 to provide a combined hydrogenation charge stream in line 81 which is cooled and charged to the hydrogenation reactor 80 at 125° C. (257° F.) to about 204° C. (400° F.) and 2.8 MPa (400 psig) to about 6.9 MPa (1000 psig). An excess of hydrogen may be employed to ensure complete saturation such as about 1.5 to about 5.0 of stochiometric hydrogen.

Hydrogenation is typically performed using a conventional hydrogenation or hydrotreating catalyst, and can include metallic catalysts containing, e.g., palladium, rhodium, nickel, ruthenium, platinum, rhenium, cobalt, molybdenum, or combinations thereof, and the supported versions thereof. Catalyst supports can be any solid, inert substance including, but not limited to, oxides such as silica, alumina, titania, calcium carbonate, barium sulfate, and carbons. The catalyst support can be in the form of powder, granules, pellets, or the like.

In an exemplary embodiment, hydrogenation is performed in the hydrogenation reactor 80 that includes a platinum-on-alumina catalyst, for example about 0.1 wt % to about 2 wt %, preferably about 0.5 wt % to about 0.9 wt %, platinum-on-alumina catalyst. In another embodiment, the hydrogenation catalyst comprises about 5 to about 30 wt % nickel catalyst. The hydrogenation reactor 80 converts the olefins into a paraffin product having the same carbon number distribution as the olefins, thereby forming distillate-range paraffins suitable for use as jet and diesel fuel.

The hydrogenated heavy stream discharged from the hydrogenation reactor 80 in line 83 may be separated in a hot separator 82 which provides a hydrocarbon split. In the hot separator 82, the hydrogenated heavy stream is separated into a hot hydrogenated vapor stream in an overhead line 84 and a hot hydrogenated liquid stream in the hot separator bottoms line 86. The hydrogenated heavy liquid stream in the bottoms line 86 may be heated by heat exchange with the diluent stream in line 14 before the diluent stream is recycled to the first-stage oligomerization reactor 22 in FIG. 1. The heated hydrogenated heavy liquid stream in the hot bottoms line 86 may be fed to a stripper column 90. The hot separator may be operated at a temperature of about 204° C. (400° F.) to about 343° ° C. (650° F.) and a pressure of 2.8 MPa (400 psig) to about 6.9 MPa (1000 psig).

The hot hydrogenated vapor stream in the hot overhead line 84 may be cooled and fed to a cold separator 88. The cold separator separates the cooled hot hydrogenated vapor stream in the hot overhead line 84 into a cold vapor hydrogenated stream in a cold overhead line 87 and a cold heavy hydrogenated liquid stream in a cold bottoms line 89. A purge stream in a purge line 85 may be taken from the cold vapor hydrogenated stream in the cold overhead line 87 and the remainder may be compressed and combined with make-up hydrogen in line 88 to provide the hydrogen stream in line 76. The cold hydrogenated heavy liquid stream in the bottoms line 89 may be fed to the stripping column 90 at a feed location above that for the hot hydrogenated heavy liquid stream in the hot separator bottoms line 86. The cold separator may be operated at a temperature of about 32° ° C. (90° F.) to about 71° C. (150° F.) and a pressure of about 2.8 MPa (400 psig) to about 4.5 MPa (650 psig).

The stripping column 90 may be a flash stripper to remove light gases from the hot hydrogenated liquid stream in the hot bottoms line 86 and the cold hydrogenated liquid stream in the cold bottoms line 89. Both of these streams can be combined and charged to the stripping column 90 or they can be charged separately as shown. The stripping column 90 removes residual light gases from the liquid hydrogenated streams to provide a stripper overhead stream in a stripper overhead line 92 and a stripped bottom stream in a stripper bottoms line 94. The stripper overhead stream in the stripper overhead line 92 is cooled and separated in a stripper receiver 96 to provide a stripper off-gas stream in a stripper receiver overhead line 97 and a condensate stream in line 98 which is refluxed to the column. The stripping column 90 may be operated at a bottoms temperature of about 232° C. (450° F.) to about 316° ° C. (600° F.) and an overhead pressure of about 207 kPa (30 psig) to about 689 kPa (100 psig).

After undergoing stripping to remove volatiles in the stripping column 90, the stripped fuel stream in the stripper bottoms line 94 may be fed to the jet fractionation column 100 without further heating. Alternatively, the stripping column 90 may be omitted upstream of the jet fractionation column 100. In the jet fractionation column 100, the stripped fuel stream may be separated into a jet off-gas stream in an overhead line 102, a green jet stream in a side line 104 from a side of the jet fractionation column 100 and a green diesel stream in a bottoms line 106. The jet fractionation column 100 may be operated at a bottoms temperature of about 288° C. (550° F.) to about 400° ° C. (750° F.) and an overhead pressure of about 35 kPa (5 psig) to about 350 kPa (50 psig).

The jet fractionation overhead stream in the overhead line 102 may be cooled and a part of the resulting condensate portion refluxed from a jet fractionation receiver 108 back to the jet fractionation column 100 in a jet fractionator overhead liquid line 109 while the remaining condensate is taken as a naphtha range product stream in line 119. Additionally, the net off gas stream comprising C4 to C8− hydrocarbons is taken in a receiver overhead line 105 from the jet fractionation receiver 108. Most of the hydrocarbons in the net off gas stream in the receiver overhead line 105 are lighter hydrocarbons and can be used to fuel the reboil heater 116 for the jet fractionation column 100.

The green jet stream taken in the side line 104 comprises kerosene range C8-C18 hydrocarbons and may be cooled and taken as a jet fuel product meeting applicable SPK standards. In an alternative embodiment, the green jet stream may be taken from the condensate stream in line 109 from the jet fractionation receiver 108 instead of refluxing all of the condensate to the column. This green jet stream taken from line 109 may have to be further stripped to remove light ends. In such an embodiment, no side line 104 would be taken to recover the green jet fuel stream.

The green diesel bottoms stream in the bottoms line 106 may be split between a reboil diesel stream in line 107 and a diesel product stream in line 114. The reboil diesel stream in line 107 may be split into the jet bottoms heat exchange stream 74 and a bypass bottoms stream in the bottoms bypass line 111. As shown in FIG. 1, the jet bottoms heat exchange stream in the jet bottoms heat exchange line 74 may be split between a first a first hot diesel stream in line 52 and a second hot diesel stream in line 73 to provide reboil heat in to the dealkanizer column 40 and the olefin splitter column 60, respectively. Either the bypass bottoms stream in line 111 through a valve thereon or the cooled second hot diesel stream in line 112 or some of both is taken in a jet reboil line 113 and reboiled in a fired heater 116 and fed back to the jet fractionation column 100.

The diesel product stream in line 114 is split between a diesel product stream in a diesel product line 118 and the diluent stream in line 14. The diluent stream in line 14 may be cooled by heat exchange with the hot hydrogenated heavy liquid stream in the hot separator bottoms line 86 and recycled back to be mixed with the charge olefin streams in lines 13*a* and 13*b* in the oligomerization section 10 in FIG. 1, preferably the first charge olefin stream in line 13*a*, to provide the first diluted olefin charge stream in line 16*a* to absorb the exotherm in the oligomerization reactor 22. The green diesel stream in the diluent line 14 is paraffinic, so it will be inert to the oligomerization and hydrogenation reactions to which it may be subject. The diesel product stream in the diesel product line 118 may be cooled and fed to the diesel pool.

Starting with ethylene and/or propylene, the disclosed process can efficiently produce Sustainable Aviation Fuel that meets applicable fuel requirements while managing exothermic heat generation. The process can also produce green gasoline and diesel byproducts that may either be used as-produced or as a blending component in fuels that meet applicable fuel requirements depending on the specific application. Carbon recovery in the process can exceed 95%. Both the jet fuel stream in the side line 104 and the diesel product stream in line 118 can be cooled and fed to their respective fuel pools.

Example

Figure 3:
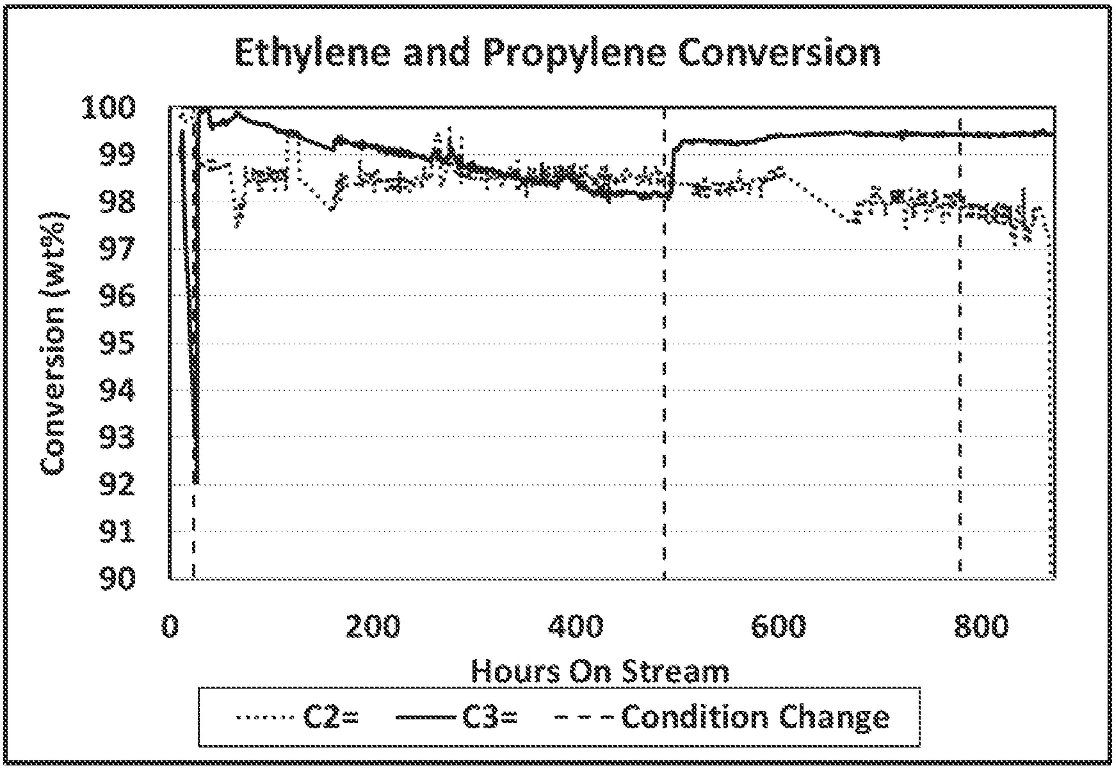
FIG. 3 is a plot of ethylene and propylene conversion over time.
Figure 4:
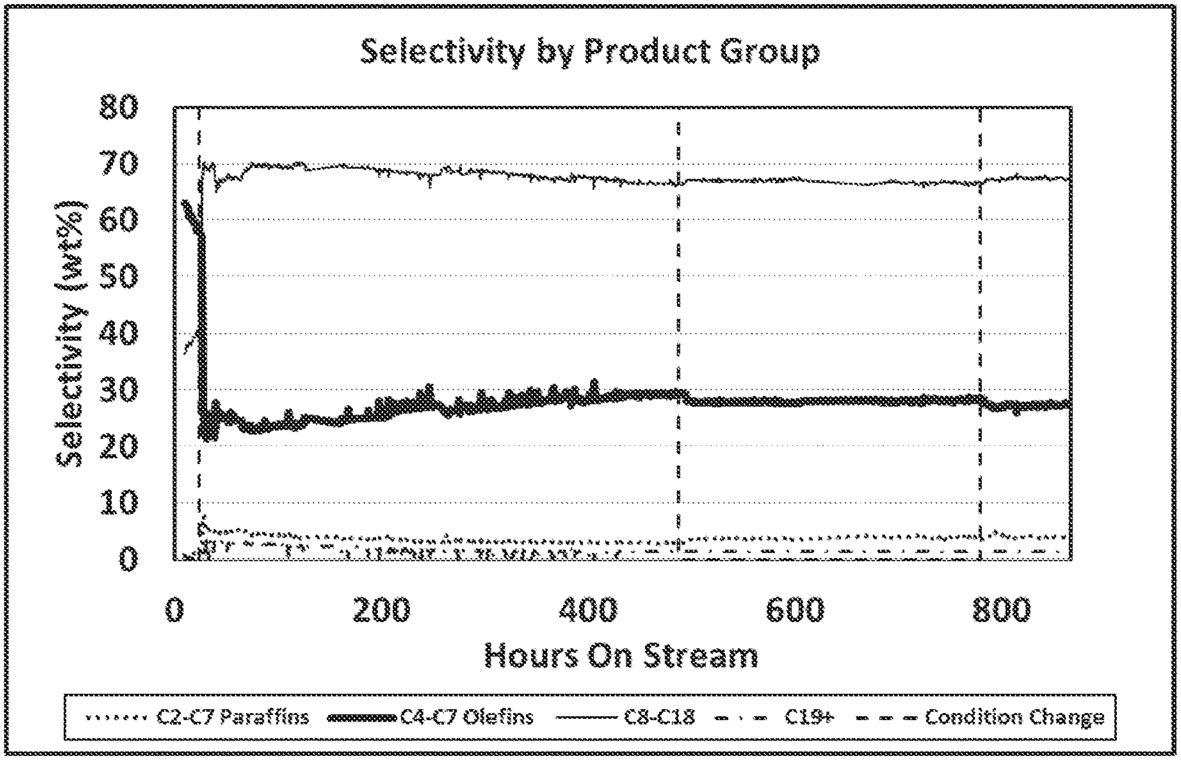
FIG. 4 is a plot of product selectivity over time.
Figure 5:
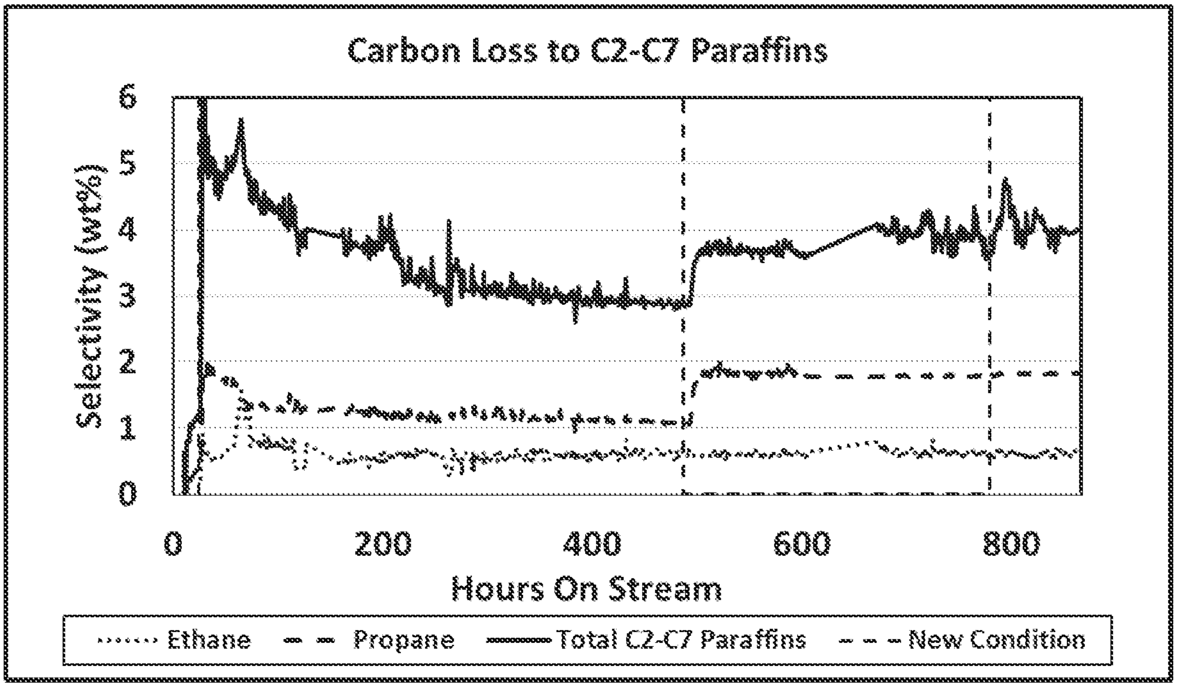
FIG. 5 is a plot of carbon loss to ethane, propane, and total C2-C7 paraffins over time.

A first stage oligomerization catalyst comprising zeolite and a second stage oligomerization catalyst comprising metal were loaded in a pilot plant reactor in a stacked bed configuration. The reactor was fed primarily with ethylene, propylene, and paraffin diluent, along with smaller amounts of C4+ olefins. The test was conducted at 6.2 MPa (gauge) (900 psig) pressure, with an inlet temperature to the first oligomerization stage catalyst varying from 160 to 250° C. and to the second oligomerization stage catalyst varying from 130 to 250° C. and WHSV in the fresh olefin charge varying from 0.25 to 2.0 $hr^{-1}$. Depending on the test conditions, the results demonstrate over 97 wt % ethylene and propylene conversion shown in FIG. 3, high jet and recyclable light olefin selectivity in FIG. 4. FIG. 5 shows the light paraffin selectivity which is approximately 3-4 wt % at steady state under these conditions. The majority consists of ethane and propane.

The oligomerization product generated in this pilot plant run was then hydrogenated and fractionated. Table 1 displays the physical properties of jet fuel which was generated from the hydrogenated oligomerization product.

TABLE 1

| Jet Fuel Property | Value |
|---|---|
| Density @ 60 F | 768.3 kg/$m^3$ |
| Flash Point | 42° C. |
| Freeze Point | <−80° C. |
| Distillation Temp (D86): T10 | 164.3 |
| Distillation Temp (D86): T50 | 197 |
| Distillation Temp (D86): T90 | 263.7 |
| Distillation Temp (D86): Final boiling point | 285.6 |

SPECIFIC EMBODIMENTS

While the following is described in conjunction with specific embodiments, it will be understood that this description is intended to illustrate and not limit the scope of the preceding description and the appended claims.

A first embodiment of the disclosure is a process for oligomerizing an olefin stream comprising oligomerizing a charge olefin stream and a recycle olefin stream over a first-stage oligomerization catalyst to produce a first-stage oligomerized stream; oligomerizing the first-stage oligomerized stream over a second-stage oligomerization catalyst to provide a second-stage oligomerized stream; and taking the recycle olefin stream from the second-stage oligomerized stream. An embodiment of the disclosure is one, any or all of prior embodiments in this paragraph up through the first embodiment in this paragraph wherein taking the recycle olefin stream comprises depropanizing the second-stage oligomerized stream to provide a light alkane stream and a depropanized stream. An embodiment of the disclosure is one, any or all of prior embodiments in this paragraph up through the first embodiment in this paragraph wherein taking the recycle olefin stream comprises splitting the second-stage oligomerized stream into a light olefin stream and a heavy olefin stream and taking the recycle olefin stream from the light olefin stream. An embodiment of the disclosure is one, any or all of prior embodiments in this paragraph up through the first embodiment in this paragraph wherein taking the recycle olefin stream further comprises splitting the depropanized stream into a light olefin stream and a heavy olefin stream and taking the recycle olefin stream from the light olefin stream. An embodiment of the disclosure is one, any or all of prior embodiments in this paragraph up through the first embodiment in this paragraph wherein taking the recycle olefin stream further comprises separating the light olefin stream to provide a light vapor stream and a light liquid overhead stream and taking the recycle olefin stream from the light liquid overhead stream. An embodiment of the disclosure is one, any or all of prior embodiments in this paragraph up through the first embodiment in this paragraph wherein taking the recycle olefin stream further comprises separating the light alkane stream to provide an off-gas stream and a light alkane condensate stream and taking the recycle olefin stream from the light alkane condensate stream. An embodiment of the disclosure is one, any or all of prior embodiments in this paragraph up through the first embodiment in this paragraph further comprising combusting the light alkane stream to provide heating requirements in the process. An embodiment of the disclosure is one, any or all of prior embodiments in this paragraph up through the first embodiment in this paragraph wherein the light alkane stream comprises a propane stream. An embodiment of the disclosure is one, any or all of prior embodiments in this paragraph up through the first embodiment in this paragraph wherein the light alkane stream comprises an ethane stream. An embodiment of the disclosure is one, any or all of prior embodiments in this paragraph up through the first embodiment in this paragraph wherein oligomerizing a charge olefin stream and a recycle olefin stream over a first-stage oligomerization catalyst further comprises oligomerizing the charge olefin stream and a first recycle olefin stream over a first-stage oligomerization catalyst in a first catalyst bed to produce a first effluent stream and oligomerizing the first effluent stream and a second recycle olefin stream over a first-stage oligomerization catalyst in a second catalyst bed. An embodiment of the disclosure is one, any or all of prior embodiments in this paragraph up through the first embodiment in this paragraph wherein oligomerizing a charge olefin stream and a recycle olefin stream over a first-stage oligomerization catalyst further comprises oligomerizing the charge olefin stream over a first-stage oligomerization catalyst in a first catalyst bed to produce a first effluent stream and oligomerizing the first effluent stream and a recycle olefin stream over a first-stage oligomerization catalyst in a second catalyst bed. An embodiment of the disclosure is one, any or all of prior embodiments in this paragraph up through the first embodiment in this paragraph further comprising hydrogenating the second-stage oligomerized stream to provide a distillate fuel stream. An embodiment of the disclosure is one, any or all of prior embodiments in this paragraph up through the first embodiment in this paragraph further comprising recycling a diluent taken from the distillate fuel stream to the oligomerizing step over the first-stage oligomerization catalyst.

A second embodiment of the disclosure is a process for oligomerizing an olefin stream comprising oligomerizing a charge olefin stream over a first-stage oligomerization catalyst in a first catalyst bed to produce a first effluent stream; oligomerizing the first effluent stream and a recycle olefin stream over a first-stage oligomerization catalyst in a second catalyst bed to produce a first-stage oligomerized stream; oligomerizing the first-stage oligomerized stream over a second-stage oligomerization catalyst to provide a second-stage oligomerized stream; and taking the recycle olefin stream from the second-stage oligomerized stream. An embodiment of the disclosure is one, any or all of prior embodiments in this paragraph up through the second embodiment in this paragraph wherein taking the recycle olefin stream comprises depropanizing the second-stage oligomerized stream to provide a light alkane stream and a depropanized stream. An embodiment of the disclosure is one, any or all of prior embodiments in this paragraph up through the second embodiment in this paragraph wherein taking the recycle olefin stream comprises splitting the second-stage oligomerized stream into a light olefin stream and a heavy olefin stream and taking the recycle olefin stream from the light olefin stream. An embodiment of the disclosure is one, any or all of prior embodiments in this paragraph up through the second embodiment in this paragraph wherein taking the recycle olefin stream further comprises splitting the depropanized stream into a light olefin stream and a heavy olefin stream and taking the recycle olefin stream from the light olefin stream. An embodiment of the disclosure is one, any or all of prior embodiments in this paragraph up through the second embodiment in this paragraph wherein taking the recycle olefin stream further comprises separating the light olefin stream to provide a light vapor stream and a light liquid overhead stream and taking the recycle olefin stream from the light liquid overhead stream. An embodiment of the disclosure is one, any or all of prior embodiments in this paragraph up through the second embodiment in this paragraph further comprising hydrogenating the second-stage oligomerized stream to provide a distillate fuel stream.

A third embodiment of the disclosure is a process for oligomerizing an olefin stream comprising oligomerizing a charge olefin stream over a first-stage oligomerization catalyst to produce a first-stage oligomerized stream; oligomerizing the first-stage oligomerized stream over a second-stage oligomerization catalyst to provide a second-stage oligomerized stream; and depropanizing the second-stage oligomerized stream to provide a light alkane stream and a depropanized stream. An embodiment of the disclosure is one, any or all of prior embodiments in this paragraph up through the third embodiment in this paragraph further comprising oligomerizing the charge olefin stream with a recycle olefin stream over the second-stage oligomerization catalyst and taking the recycle olefin stream from the depropanized stream. An embodiment of the disclosure is one, any or all of prior embodiments in this paragraph up through the third embodiment in this paragraph wherein taking the recycle olefin stream from the depropanized stream further comprises splitting the depropanized stream into a light olefin stream and a heavy olefin stream and taking the recycle olefin stream from the light olefin stream. An embodiment of the disclosure is one, any or all of prior embodiments in this paragraph up through the third embodiment in this paragraph wherein taking the recycle olefin stream from the light olefin stream further comprises separating the light olefin stream to provide a light off-gas stream and a light liquid overhead stream and taking the recycle olefin stream from the light liquid overhead stream.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for oligomerizing an olefin stream comprising:

oligomerizing a charge olefin stream and a recycle olefin stream over a first-stage oligomerization catalyst to produce a first-stage oligomerized stream;

oligomerizing said first-stage oligomerized stream over a second-stage oligomerization catalyst to provide a second-stage oligomerized stream;

taking said recycle olefin stream from said second-stage oligomerized stream, and wherein taking said recycle olefin stream comprises deethanizing or depropanizing said second-stage oligomerized stream to provide a light alkane stream and a deethanized or a depropanized stream.

2. The process of claim 1 wherein taking said recycle olefin stream comprises depropanizing said second-stage oligomerized stream to provide a light alkane stream and a depropanized stream.

3. The process of claim 1 wherein taking said recycle olefin stream comprises splitting said second-stage oligomerized stream into a light olefin stream and a heavy olefin stream and taking said recycle olefin stream from said light olefin stream.

4. The process of claim 2 wherein taking said recycle olefin stream further comprises splitting said depropanized stream into a light olefin stream and a heavy olefin stream and taking said recycle olefin stream from said light olefin stream.

5. The process of claim 4 wherein taking said recycle olefin stream further comprises separating said light olefin stream to provide a light vapor stream and a light liquid overhead stream and taking said recycle olefin stream from said light liquid overhead stream.

6. The process of claim 2 wherein taking said recycle olefin stream further comprises separating said light alkane stream to provide an off-gas stream and a light alkane condensate stream and taking said recycle olefin stream from said light alkane condensate stream.

7. The process of claim 2 further comprising combusting said light alkane stream to provide heating requirements in said process.

8. The process of claim 2 wherein said light alkane stream comprises a propane stream.

9. The process of claim 2 wherein said light alkane stream comprises an ethane stream.

10. The process of claim 1 wherein oligomerizing a charge olefin stream and a recycle olefin stream over a first-stage oligomerization catalyst further comprises oligomerizing said charge olefin stream and a first recycle olefin stream taken from the recycle olefin stream, over a first-stage oligomerization catalyst in a first catalyst bed to produce a first effluent stream and oligomerizing said first effluent stream and a second recycle olefin stream over a first-stage oligomerization catalyst in a second catalyst bed.

11. The process of claim 1 wherein oligomerizing a charge olefin stream and a recycle olefin stream over a first-stage oligomerization catalyst further comprises oligomerizing said charge olefin stream over a first-stage oligomerization catalyst in a first catalyst bed to produce a first effluent stream and oligomerizing said first effluent stream and a recycle olefin stream over a first-stage oligomerization catalyst in a second catalyst bed.

12. The process of claim 1 further comprising hydrogenating said second-stage oligomerized stream to provide a distillate fuel stream.

13. The process of claim 10 further comprising recycling a diluent taken from said distillate fuel stream to said oligomerizing step over said first-stage oligomerization catalyst.

14. A process for oligomerizing an olefin stream comprising:

oligomerizing a charge olefin stream over a first-stage oligomerization catalyst in a first catalyst bed to produce a first effluent stream;

oligomerizing said first effluent stream and a recycle olefin stream over a first-stage oligomerization catalyst in a second catalyst bed to produce a first-stage oligomerized stream;

oligomerizing said first-stage oligomerized stream over a second-stage oligomerization catalyst to provide a second-stage oligomerized stream; and taking said recycle olefin stream from said second-stage oligomerized stream.

15. The process of claim 14 wherein taking said recycle olefin stream comprises depropanizing said second-stage oligomerized stream to provide a light alkane stream and a depropanized stream.

16. The process of claim 14 wherein taking said recycle olefin stream comprises splitting said second-stage oligomerized stream into a light olefin stream and a heavy olefin stream and taking said recycle olefin stream from said light olefin stream.

17. The process of claim 15 wherein taking said recycle olefin stream further comprises splitting said depropanized stream into a light olefin stream and a heavy olefin stream and taking said recycle olefin stream from said light olefin stream.

18. The process of claim 17 wherein taking said recycle olefin stream further comprises separating said light olefin stream to provide a light vapor stream and a light liquid overhead stream and taking said recycle olefin stream from said light liquid overhead stream.

19. The process of claim 14 further comprising hydrogenating said second-stage oligomerized stream to provide a distillate fuel stream.

20. A process for oligomerizing an olefin stream comprising:

oligomerizing a charge olefin stream over a first-stage oligomerization catalyst to produce a first-stage oligomerized stream;

oligomerizing said first-stage oligomerized stream over a second-stage oligomerization catalyst to provide a second-stage oligomerized stream; and depropanizing said second-stage oligomerized stream to provide a light alkane stream and a depropanized stream.

21. The process of claim 20 further comprising oligomerizing said charge olefin stream with a recycle olefin stream over said second-stage oligomerization catalyst and taking said recycle olefin stream from said depropanized stream.

22. The process of claim 21 wherein taking said recycle olefin stream from said depropanized stream further comprises splitting said depropanized stream into a light olefin stream and a heavy olefin stream and taking said recycle olefin stream from said light olefin stream.

23. The process of claim 22 wherein taking said recycle olefin stream from said light olefin stream further comprises separating said light olefin stream to provide a light off-gas stream and a light liquid overhead stream and taking said recycle olefin stream from said light liquid overhead stream.

* * * * *